(12) United States Patent
Frank et al.

(10) Patent No.: US 7,049,282 B2
(45) Date of Patent: May 23, 2006

(54) INHIBITION OF COMPLEMENT ACTION

(75) Inventors: Michael M. Frank, Durham, NC (US); Haixiang J. Jiang, Chapel Hill, NC (US)

(73) Assignee: Duke University, Durham, NC (US)

( * ) Notice: Subject to any disclaimer, the term of this patent is extended or adjusted under 35 U.S.C. 154(b) by 127 days.

(21) Appl. No.: 09/984,017

(22) Filed: Oct. 26, 2001

(65) Prior Publication Data
US 2002/0115614 A1    Aug. 22, 2002

Related U.S. Application Data

(63) Continuation of application No. PCT/US00/10928, filed on Apr. 25, 2000.

(60) Provisional application No. 60/130,936, filed on Apr. 26, 1999.

(51) Int. Cl.
*A01N 37/18*    (2006.01)

(52) U.S. Cl. .................. 514/2; 514/21; 514/2; 514/14; 514/15

(58) Field of Classification Search ............ 514/2, 514/21, 14, 15

See application file for complete search history.

(56) References Cited

U.S. PATENT DOCUMENTS

| | | | | |
|---|---|---|---|---|
| 4,753,927 A | * | 6/1988 | Hahn | 514/13 |
| 5,726,286 A | | 3/1998 | Alderson et al. | 530/300 |
| 5,731,168 A | * | 3/1998 | Carter et al. | 435/69.1 |
| 5,869,286 A | | 2/1999 | Yao et al. | 435/69.1 |
| 6,451,308 B1 | * | 9/2002 | Strom et al. | 424/134.1 |

FOREIGN PATENT DOCUMENTS

| | | |
|---|---|---|
| WO | WO 95/30015 | * 11/1995 |
| WO | WO 98/31820 | 7/1998 |

OTHER PUBLICATIONS

Linton et al, "Complement Activation and Inhibition in Experimental Models of Arthritis", Molecular Immunology 36:905-914 (1999).

Nielsen et al, "The Role of Complement in the Acquired Immune Response", Immunology 100:4-12 (2000).

Platt et al, "The Role of Complement in Transplantation", Molecular Immunology 36:965-971 (1999).

* cited by examiner

*Primary Examiner*—Kathleen M. Kerr
*Assistant Examiner*—Hope Robinson
(74) *Attorney, Agent, or Firm*—Nixon & Vanderhye P.C.

(57) ABSTRACT

The present invention relates to a method of blocking biochemical function of the classical complement pathway and thereby preventing immunologic damage in a variety of diseases and conditions including autoimmune diseases.

13 Claims, No Drawings

INHIBITION OF COMPLEMENT ACTION

This application is a continuation of Application No. PCT/US00/10928, filed Apr. 25, 2000, which claims benefit of Provisional Application No. 60/130,936, filed Apr. 26, 1999, the entire contents of which are hereby incorporated herein reference.

The present invention was made with Government support under Grant No. 5RO1AI35033-05 (National Institutes of Health) and PO1 HL50985-05 (National Institutes of Health). The Government may have certain rights in the invention.

TECHNICAL FIELD

The present invention relates to a method of blocking biochemical function of the complement pathway and thereby preventing immunologic damage in a variety of diseases (including autoimmune diseases) and conditions. The invention also relates to a method of preventing hyperacute xenograft rejection. Further, the invention relates to agents suitable for use in such methods.

BACKGROUND

Complement is believed to play a major role in host defense against infection. In general, complement causes damage by three mechanisms. For certain targets, interaction of the complement proteins with the target cell or microorganism causes direct lysis of that microorganism or cell. In a second series of reactions, complement proteins deposited on cells or microorganisms interact with a series of specific receptors on phagocytes that aid in the phagocytic process, thus removing the pathologic cell or microorganism from the body. Complement activation also leads to the generation of a series of activation peptides that are capable of producing inflammation. In addition, complement is thought to play a major role in the afferent limb of the immune response, increasing the immunogenicity of antigens with bound complement peptides. It may also be important in eliminating clones of lymphocytes involved in the immune response to self antigens.

It is believed that the major efferent functions of complement are, in part, responsible for some of the symptomatology in autoimmune disease. In autoimmune diseases, antigens on an individual's own tissues (self antigens) within the body become immunogenic and induce an immune response, for reasons that are not fully understood. One of the mechanisms in damaging the host's cells or tissues is activation of the complement system by antibody with resulting destruction of the cells or tissues. Another mechanism is the formation of or deposition of immune complexes within tissues with the activation of complement and the production of inflammation.

There are three pathways of complement activation that have been identified: the lectin pathway, the classical pathway, and the alternative pathway (details of pathway function are published elsewhere, e.g., in The Human Complement System in Health and Disease, Volanakis and Frank (eds), Marcel Dekker, Inc. (1998)). The lectin pathway appears to be a primative pathway induced by a series of lectin like molecules, such as mannan binding lectin (MBL) These proteins bind to the surface of microorganisms with the appropriate sugar moiety on their surface and activate a series of enzymes. This in turn leads to activation of complement and the destructive process described above.

In the classical pathway, specific antibody is formed to either tissues, other body constituents, or to microorganisms. In turn, this recruits a series of complement proteins termed C1, C4, and C2, to form an enzyme capable of activating C3 and the later proteins of the complement cascade. This activation pathway leads to the above-described pathologic consequences.

The third pathway is termed the alternative pathway Here, complement proteins are capable of interacting with activators of the alternative pathway, such as microorganism surfaces. These proteins can be deposited on the surface of certain microorganisms in the absence of specific antibody. The later acting complement proteins are recruited leading to damage.

The lectin pathway is a relatively recent discovery, but the alternative and classical pathways have been studied for some years. It is believed that the alternative pathway is a philogenetically older pathway that does not have an absolute requirement of antibody to function. It would appear that the classical pathway evolved to provide a higher degree of specificity and sensitivity to the damage producing complement related steps.

Thus, antibody can target tissues for destruction. In certain autoimmune diseases, this leads to specific destruction of a patient's own tissue. The advantage of blocking the classical pathway and not the alternative pathway is that the alternative pathway provides a first line of defense against microorganisms. It is believed that because the alternative pathway does not require antibody, patients with an intact alternative pathway are relatively protected against overwhelming infection. The classical pathway, in some autoimmune diseases, is of particular importance since antibody to host tissue or various released tissue components can activate the classical pathway and initiate damage. Thus, blocking the classical pathway in some diseases may lead to specific interruption of the pathophysiologic sequence leading to tissue damage and disease. If this could be done with an alternative pathway relatively intact, it would lead to blocking of the pathophysiologic sequence, without subjecting the patient to an unacceptable risk of infection. Nonetheless, there may be situations in which blocking of the alternative pathway alone, or both the alternative and classical pathways, is preferable.

It was reported previously that intravenous immunoglobulin blocks the binding of C3 to target tissues. Subsequently, it was reported that not only is C3 binding to target tissues blocked by high levels of monomeric immunoglobulin, but C4 binding to target tissues is blocked as well. There are data that suggest that since C4 must be activated and must bind to a target before C3, it is the blocking of C4 binding that is central to classical pathway inhibition. Further research has now shown that this blockade is due to activity of the Fc fragment of the IgG.

The present invention results, at least in part, from the demonstration that peptides can be isolated from digests of the Fc fragment of IgG that retain the complement blocking activity shown in intact immunoglobulins.

DETAILED DESCRIPTION OF THE INVENTION

The present invention relates, generally, to agents that block the biochemical function of the complement pathways and to a method of preventing immunologic damage using same. More specifically, the invention relates to agents that have a complement blocking activity similar to that of the Fc fragment of IgG and to the use thereof in treating autoimmune diseases and in preventing hyperacute xenograft rejection. The invention includes methods of using such agents to prevent tissue damage caused by complement activation generally.

Agents of the present invention include peptide fragments of the Fc fragment of IgG that retain the complement blocking activity of intact immunoglobulin, as well as derivatives of such peptides and mimetics thereof that have complement blocking activity.

The peptides of the invention are, preferably, 5 to 100 amino acids in length, more preferably, 10 to 50 amino acids in length. The peptides can be isolated for digest of the Fc fragment of IgG or they can be chemically synthesized using standard protocols. Examples of suitable peptides include the sequences WESNGQPENN (SEQ ID NO:1) (approximately residues 381 to 390 of the IgG sequence) and KTISKAKGQPREPQVYT (SEQ ID NO:2) (corresponding to approximately residues 334–351 of the IgG sequence). (One full length sequence of IgG was reported by Edelman et al, Proc. Nat. Acad. Sci. USA 63:78–85 (1969), the numbering of the first amino acid of the specific peptides referenced here conforms to the numbering of Edelman et al (residue numbering may vary in other published sequences).) Further peptides suitable for use in the invention, for example, peptides from the $CH_2$ and $CH_3$ domains of IgG, as well as the $CH_2$, $CH_3$ and $CH_4$ domains of IgM, can be identified using methods set forth in the Examples that follow.

Agents of the invention also include derivatives of the above-described peptides. These derivatives can have one or more amino acid substitutions, deletions or insertions relative to peptides derived from IgG or IgM, while still having complement blocking activity. It will be appreciated by the skilled person that high degrees of sequence identity (e.g., as determined by the BLAST program) are not necessarily required since various amino acids can be substituted for other amino acids that have similar properties without substantially altering or adversely affecting biological properties. These constitute "conservative" amino acid changes. The amino acids glycine, valine, leucine and isoleucine can be substituted for one another; similarly, phenylalanine, tyrosine and tryptophan (amino acids having aromatic side chains) can be substituted for one another; likewise, lysine, arginine and histidine (amino acids having basic side chains), aspartate and glutamate (amino acids having acidic side chains), asparagine and glutamine (amino acids having amide side chains) and cysteine and methionine (amino acids having sulphur containing side chains). Thus the derivatives of the invention include variants of the amino acid sequences of the peptides of the invention, which variants have an amino acid sequence comprising one or more such conservative changes relative to the sequence of the corresponding peptide derived from IgG or IgM. Preferably, the degree of sequence identity between a derivative of the invention and the corresponding peptide is at least 50%, and more preferably at least 75%, most preferably, at least 90% or 95%, as determined using the above-described program.

The complement blocking activity of both the peptides and derivatives of the invention can be significantly enhanced by coupling such agents to neutral proteins, such as serum albumin, that do not themselves have complement regulatory activity. The coupling can be effected using known chemical techniques or it can be effected by recombinantly producing the coupled product. For example, the above-referenced 10 amino acid peptide coupled to bovine serum albumin using glutaraldehyde had a complement blocking activity 10–20 times that of the non-coupled peptide.

In addition to the peptides and derivatives described above, the invention also relates to mimetics of the peptides that have the above-described complement blocking function. The mimetics can be identified using protocols available in the art, including those described by Miletic et al, J. Immunology 156:749 (1996)) which are based on the binding of complement to antibody-sensitized red blood cells and on the binding of complement to solid phase immune complexes. As described below, these protocols can be used to identify complement-blocking peptides and derivatives as well.

Peptides, derivatives and mimetics that block complement function can be identified by incubating a target for an active complement protein, for example, antibody-coated particles (e.g., antibody-sensitized red blood cells) or immune complexes (e.g., bovine serum albumin-anti-bovine serum complexes) bound to a solid support, with the a complement protein or a complement activating system (e.g., containing C3 or C4 or mixtures of complement proteins such as found in serum (e.g., C8 or C9 deficient serum)), in the presence and in the absence of the test agent (peptide, derivative or mimetic). The incubation is carried out under conditions such that the complement protein can bind the target in the absence of the test agent. The amount of binding of the complement protein to the target that occurs in the absence of the test agent is compared to the amount of binding that occurs in the presence of the test agent. A test agent that inhibits binding of the complement protein to the target in this assay is an agent that blocks complement binding. The amount of binding can be determined using any of a variety of approaches, including using radiolabeled anti-complement protein IgG. Alternatively, the complement protein can be labeled (e.g., radiolabeled) and the ability of the test agent to compete with the labeled complement protein for binding to the target determined. Other methods of determining the extent of complement binding are also available and can be used.

The peptides, derivatives and mimetics of the invention are useful in therapeutic and prophylactic contexts. As indicated above, complement binding can account for substantial tissue damage in a wide variety of autoimmune/immune complex mediated syndromes such as systemic lupus erythematosus, vasculitis, hemolytic anemias, myasthenia gravis and others. Inhibition of the complement system is likely to be desirable therapeutic intervention in these cases. These peptides can also be used to inhibit complement activation, which is desirable in cases that involve tissue damage brought about by vascular injury such as myocardial infarction, cerebral vascular accidents or acute shock lung syndrome. In these cases, the complement system may contribute to the destruction of partially damaged tissue as in reperfusion injury.

Complement inhibition is also important in the prevention of xenograft rejection. The agents of the invention can be used in xenotransplantations involving various species combinations. Clinically relevant combinations include porcine to primate and primate to primate combinations. More specifically, the agents of the invention can be used to suppress xenograft rejections wherein the donor is a porcine or primate donor and the recipient is a human. The donor can be a nontransgenic animal or transgenic animal that expresses recipient complement inhibitory proteins on cell surfaces of the donated organ. In either case, the agent can be used to suppress hyperacute rejection of tissues including heart, lung, liver, kidney.

The dosage level and mode of administration of the agents of the invention depend on the nature of the agent, the nature of the condition to be treated, and the history of the individual patient. Optimum doses can be readily determined by one skilled in the art.

Systemic administration of the peptide, derivative or mimetic of the invention is generally required which may be by injection or by transmucosal or transdermal delivery. Administration by injection may be intravenous, intramuscular, intraperitoneal or subcutaneous.

The invention further relates to pharmaceutical compositions (formulations) comprising the agent of the invention and a pharmaceutically acceptable carrier. Formulations for injection are generally biocompatible solutions of the active ingredient, such as Hank's solution, Ringer's solution or saline. Formulations for transdermal or transmucosal administration generally include penetrants such as fusidic acid or bile salts in combination with detergents or surface-active agents. The formulations can then be manufactured as aerosols, suppositories, or patches. Oral administration is generally not favored for peptide active ingredients; however, if suitably formulated so as to be protected from the digestive enzymes, oral administration can also be employed. Suitable formulations for a desired mode of administration can be found in Remington's Pharmaceutical Sciences, latest edition, Mack Publishing Co., Easton, Pa.

Certain aspects of the present invention are described in greater detail in the non-limiting Examples that follow.

EXAMPLE 1

Fragment of IgG Responsible for Inhibition of Complement Binding

IgG fragments were prepared by incubation of IgG solutions with insolubilized papain bound to agarose. IgG incubated with papain forms Fab and Fc fragments and these were isolated to purity. It was found that all of the activity of intact IVIG was localized to the Fc fragment. There was no activity in the Fab or F(ab)$'_2$ fragment formed by digestion of the antibody molecules. Pepsin bound agarose beads were also utilized. In this case, the Fc fragment of IgG is digested into small peptides with the resulting F(ab)$'_2$ fragment of IgG formed.

The Fc fragments of IgG prepared by papain were digested with insolubilized pepsin. In this case, the Fc fragment is digested to small peptides. In later experiments, intact IgG was incubated with insolubilized pepsin. As expected, small peptides were generated. The material was then passed through a FPLC Superose 12 column which separates intact IgG and F(ab)$'_2$ from the smaller peptides. Protein G Sepharose was used in addition to remove intact IgG and intact Fc from small peptides. Active peptide fractions were further separated on a Sephadex peptide column. It was possible to isolate two peptides by HPLC hydrophobic chromatography and to determine the sequence of these two peptides by both mass spectrometry examining various peptide fragments after electron bombardment and by more conventional sequencing techniques. The peptides were tested for activity in the standard system (i.e., Miletic et al, J. Immunol. 156:749 (1996)) using sheep erythrocytes sensitized with rabbit antibody, and C8D human serum. Highly active preparations of small peptides were recovered that inhibited markedly complement binding to the sheep erythrocyte targets.

Experiments were performed with both pepsin digested Fc fragments and peptides obtained from pepsin digested intact IgG. Considerable variability in peptides was obtained, although inhibitory peaks always chromatographed in one general location.

To clarify the situation further, myeloma IgG was obtained by plasmapheresis from a patient with multiple myeloma. It was reasoned that pooled immunoglobulin would contain multiple subclasses of IgG and multiple possible allotypes. A single myeloma protein would generate fewer and more consistent peptides on digestion. The IgG myeloma protein was purified to homogeneity and subjected to the same digestion procedure. Inhibitory peptides were isolated and one was studied in greater detail. The peptide is in a highly exposed, hydrophilic portion of the CH3 domain. Mass spectrometry yielded a peptide with a mass of 1174. Direct microsequence analysis of the peptide and microsequencing by tandem mass spectrometry yielded a sequence that is identical to residue 381–390 (WESNGQPENN) of the IgG CH3 domain of model peptide IgG 1). This peptide is highly active in inhibiting complement binding. A peptide with this sequence was synthesized commercially and proved to be highly active in complement inhibition. A peptide was synthesized with the same amino acids but in a disordered sequence. This peptide though not totally inactive had far lower activity. In addition, other peptides from the CH3 region of IgG were synthesized and proved to be inactive.

Peptides can be synthesized with the desired amino acid sequence with various added amino acid sequences. A peptide has been generated with an added cysteine in the C terminal position and it retains full activity.

EXAMPLE 2

Definition of Peptide Responsible for Inhibition of Complement Binding

IgG is prepared from purified IVIG or from myeloma plasma by caprylic acid, ammonium sulfate precipitation and extensive dialysis and QAE chromatography if needed. At a concentration of 100 mg/ml, it is incubated with insolubilized pepsin. After digestion for 24 hours at 37° C. in pH 3.2, 0.1 M citrate buffer, the material is sedimented at 3,000 rpm in a Sorvall centrifuge. The supernatant is pass through centricon 30 membrane (Amicon Co.) to separate intact IgG and $F(ab)_2$ from smaller fragments. The smaller peptides are collected, concentrated and equilibrated in VBS buffer by passage through a Pharmacia sephadex FPLC peptide column and the peptides peaks collected. These peptides are tested for inhibition of complement binding in the standard assay. For further purification and sequencing, HPLC column chromatography using a C18 hydrophobic column in 0.1% acetonitrile buffer. Active peaks are collected, their activity determined, and they are subjected to amino acid microanalysis and tandem mass spectrometry to determine amino acid sequence and molecular weight. Peptides corresponding to the active sequences on analysis are synthesized commercially with control peptides with scrambled sequence. Peptides with the active sequence and N-terminal tyrosine or C terminal or N terminal cysteine are synthesized to aid in radioiodination. In the case of N terminal cysteine, it is known that the peptide remains fully active. $^{14}C$ iodoacetamide can be used to alkylate the C terminal cysteine and the activity of the peptide can be determined. The use of spacers for the tyrosine will be explored. If the latter approach also proves unsuccessful, Bolten-Hunter reagent can be used to label amino groups directly or after introduction of spacer amino acids and lysine. C14 amino acids can be used for peptide synthesis to facilitate analysis and turnover studies.

All documents cited above are hereby incorporated in their entirety by reference.

One skilled in the art will appreciate from a reading of this disclosure that various changes in form and detail can be made without departing from the true scope of the invention.

What is claimed is:

1. A method of blocking a complement pathway in a patient in need thereof comprising administering to said patient a complement pathway blocking amount of the peptide WESNGQPENN (SEQ ID NO:1) or KTISKAKGQPREPQVYT (SEQ ID NO:2), so that said blocking is effected.

2. The method according to claim 1 wherein said patient suffers from an autoimmune disease.

3. The method according to claim 1 wherein blocking of said complement pathway reduces immunologic tissue damage in said patient, in comparison to immunologic tissue damage that results if said peptide is not administered.

4. The method according to claim 1 wherein said patient is a recipient of a xenograft and blocking of said complement pathway reduces hyperacute rejection of said xenograft, in comparison to hyperacute rejection that result if said peptide is not administered.

5. A peptide consisting of the sequence WESNGQPENN (SEQ ID NO:1).

6. A peptide consisting of the sequence KTISKAKGQPREPQVYT (SEQ ID NO:2).

7. A composition comprising the peptide according to claim 5 and a pharmaceutically acceptable carrier.

8. A composition comprising the peptide according to claim 6 and a pharmaceutically acceptable carrier.

9. A method of blocking a complement pathway in a patient in need thereof comprising administering to said patient a complement blocking amount of a peptide consisting the sequence of SEQ ID NO:1 or SEQ ID NO:2, further comprising a radiolabeled C or N terminal cysteine, so that said blocking is effected.

10. The method according to claim 9, wherein the peptide of SEQ ID NO:1, further comprising a radiolabeled C or N terminal cysteine, is administered.

11. A composition comprising the peptide of SEQ ID NO:1 or the peptide SEQ ID NO:2, wherein said peptide is coupled to a protein.

12. The composition according to claim 11 wherein said protein is serum albumin.

13. The composition according to claim 11 wherein said peptide is coupled to said protein with glutaraldehyde.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: CH2 or CH3
      domain of IgG

<400> SEQUENCE: 1

Trp Glu Ser Asn Gly Gln Pro Glu Asn Asn
 1               5                  10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: CH2 or CH3
      domain of IgG

<400> SEQUENCE: 2

Lys Thr Ile Ser Lys Ala Lys Gly Gln Pro Arg Glu Pro Gln Val Tyr
 1               5                  10                  15

Thr